US010702695B2

(12) United States Patent
Costanzo et al.

(10) Patent No.: US 10,702,695 B2
(45) Date of Patent: Jul. 7, 2020

(54) WIRELESS IMPLANTABLE TASTE SYSTEM

(71) Applicant: VIRGINIA COMMONWEALTH UNIVERSITY, Richmond, VA (US)

(72) Inventors: Richard M. Costanzo, Manakin Sabot, VA (US); Woon-Hong Yeo, Glen Allen, VA (US)

(73) Assignee: Virginia Commonwealth University, Richmond, VA (US)

( * ) Notice: Subject to any disclaimer, the term of this patent is extended or adjusted under 35 U.S.C. 154(b) by 717 days.

(21) Appl. No.: 15/247,010

(22) Filed: Aug. 25, 2016

(65) Prior Publication Data

US 2017/0087363 A1    Mar. 30, 2017

Related U.S. Application Data

(60) Provisional application No. 62/233,453, filed on Sep. 28, 2015.

(51) Int. Cl.
| | |
|---|---|
| A61N 1/36 | (2006.01) |
| A61N 1/05 | (2006.01) |
| G09B 21/00 | (2006.01) |
| G16H 20/60 | (2018.01) |
| A61B 5/00 | (2006.01) |
| G09B 19/00 | (2006.01) |

(52) U.S. Cl.
CPC ......... *A61N 1/3606* (2013.01); *A61N 1/0548* (2013.01); *A61N 1/36139* (2013.01); *G09B 21/00* (2013.01); *G16H 20/60* (2018.01); *A61B 5/682* (2013.01); *G09B 19/0092* (2013.01)

(58) Field of Classification Search
CPC ............................ A61N 1/3606; G16H 20/60

USPC ....................................................... 607/134
See application file for complete search history.

(56) References Cited

U.S. PATENT DOCUMENTS

| 4,637,405 A * | 1/1987 | Brenman ........... A61N 1/36014 |
|---|---|---|
| | | 607/134 |
| 5,482,855 A | 1/1996 | Yamafuji et al. |
| 5,789,250 A | 8/1998 | Ikezaki |

(Continued)

OTHER PUBLICATIONS

Kobayashi et al., "Advanced taste sensors based on artificial lipids with global selectivity to basic taste qualities and high correlation to sensory scores", Sensor 2010, 10, 3411-3443.

(Continued)

*Primary Examiner* — Nadia A Mahmood
(74) *Attorney, Agent, or Firm* — W&C, IP

(57) ABSTRACT

The system includes various embodiments of components, including (1) a sensor array, (2) a processor, (3) a transmitter, (4) a receiver-stimulator, and (5) an implantable electrode array. The gustatory implant system generates tastant fingerprints by detecting tastants with an array of chemical sensors and then transmitting variable spatiotemporal stimulation patterns for an electrode array with electrode stimulating points positioned at different locations in the gustatory cortex (e.g., stimulating the chorda tympanic nerve). Different patterns of activity in the gustatory cortex are thereby generated which mimic the sense of taste in a subject. Once trained the system should be usable by a subject to detect or correctly identify or perceive one or more tastes. The system may also include an external electronic device for processing and displaying information to monitor ingestion of various substances in a subject.

14 Claims, 11 Drawing Sheets

(56) References Cited

U.S. PATENT DOCUMENTS

| | | |
|---|---|---|
| 7,090,805 B2 | 8/2006 | Harada |
| 7,947,508 B2 | 5/2011 | Tricca et al. |
| 8,898,069 B2 | 11/2014 | Hood |
| 2014/0349256 A1* | 11/2014 | Connor .............. G09B 19/0092 434/127 |
| 2015/0126873 A1 | 5/2015 | Connor |

OTHER PUBLICATIONS

Arefin et al., "An artificial tongue for taste sensor based on neural network" IJCIT, ISSN 2218-5223 (online), vol. 2, issue 1, pp. 8-1.
Li et al., "Sensor-Embedded teeth for Oral Activity Recognition", ISWC'13, Sep. 9-12, 2013; Zurich, Switzerland, pp. 41-44.

* cited by examiner

WIRELESS IMPLANTABLE TASTE SYSTEM

CROSS-REFERENCE TO RELATED APPLICATIONS

This application claims the benefit of U.S. provisional patent application 62/233,453, filed Sep. 28, 2015, the complete contents of which is hereby incorporated by reference.

BACKGROUND OF THE INVENTION

Field of the Invention

The present invention generally relates to prosthetic devices and, more particularly, to wireless implantable taste systems for individuals who have an impaired or lost sense of taste.

Background Description

Information is transmitted in the human body by the nervous system. Electrical pulses, or propagating action potentials, travel along the extensions (axons) of a nerve cell, from one nerve to another (or between many nerves) to create a functional network of communication. Electric pulses begin when the organs of sensation are stimulated. While much of the perception associated with taste or gustation is actually mediated through the sense of smell or olfaction, there remains a component of taste that can be accounted for only through innervation from the taste buds to the brain. Substances in the mouth dissolve in saliva where they are known as tastants. Tastants encounter the taste buds and interact with cell surface receptors to stimulate nerves. The anterior two-thirds of the tongue are innervated by the chorda tympani branch of the facial nerve, and the posterior one-third of the tongue is innervated by the glossopharyngeal nerve. Taste buds are also found on the soft palate, pharynx, larynx, epiglottis, and first one-third of the esophagus, where the greater superficial petrosal nerve innervates the palate, and the vagus innervates the pharynx and larynx. Complete loss of gustation, or ageusia, occurs less frequently than partial loss or hypogeusia; redundancy of innervation of the gustatory system may account for this.

A large number of substances and disease processes may impact the sense of taste or gustation. Taste dysfunction may affect any one or all aspects of taste (sweetness, bitterness, sourness, saltiness, and umami). Toxic substances may cause taste dysfunction from their effects on the gustatory system from the salivary gland, to the taste bud, to the central neural pathways. A number of external toxins, including industrial compounds, tobacco, and alcohol, may adversely affect taste, most commonly through local effects in the oral cavity. Blood-borne toxins, such as medications and those present in autoimmune and other systemic disorders (e.g. renal or liver failure), have access to all parts of the gustatory system, and thus may exhibit varied effects on taste function. Many patients with various diseases develop taste disorders, including taste loss and taste distortion. Gustation frequently declines during aging, along with olfaction. Taste disorders have been implicated in loss of appetite, unintended weight loss, malnutrition, and reduced quality of life. While treatment of an underlying disease or toxic state may provide some restoration of the sense of taste, there is no treatment when lost or impaired taste function is the primary diagnosis.

Sensors and systems for detection and identification of gustatory molecules are known, and are sometimes referred to as "electronic tongues". These are primarily found in industrial or research settings, and are used for objective taste analysis or quality control of a broad range of foods, beverages, and pharmaceutical products. Another common use of electronic tongues is as an aide in the development of artificial flavorings by identifying or replicating a particular flavor or complex taste "profile" that would be perceived as being a particular food substance when consumed by a human (i.e., a "banana" flavor). Examples of these may be found in the review by Kobayashi et al., entitled "Advanced taste sensors based on artificial lipids with global selectivity to basic taste qualities and high correlation to sensory scores", in *Sensors* 2010, 10, 3411-3443. Other examples are found in U.S. Pat. No. 7,090,805 B2 to Harada, U.S. Pat. No. 5,482,855 to Yamafuji et al., and U.S. Pat. No. 5,789,250 to Ikezaki, which are drawn to analytical instruments comprising sensors that measure capacitance of a solution. An array of capacitance changes of such sensors can be combined to assess various taste qualities imparted by a solute, such as "richness" or "sharpness", components of the taste experienced by humans as being bitter. Additional sensor types are known, such as nanostructured films of conducting polymers to measure signal transduction via impedance spectroscopy, which can detect trace amounts of tastants or inorganic contaminants in a liquid, such as commercial beverages, wines, and waters (Riul et al., "An artificial taste sensor based on conducting polymers", *Biosens Bioelectron.* 2003 Oct. 1; 18(11):1365-9). Integration of data from artificial tongues can be based on neural networks to more closely replicate and represent the taste profiles of whole foodstuffs such as beer, coffee, milk, and so on, to understand complex interactions of tastes as experienced by humans, such as combinations of sweet and bitter in which a so-called suppression effect occurs (Arefin and Saha, "An artificial tongue for taste sensor based on neural network" IJCIT, ISSN 2218-5223 (online), Vol. 2, issue 1, ppb-13).

Wearable or implantable devices have been designed to monitor a person's food consumption or health status. U.S. Pat. No. 8,898,069 B2 to Hood et al. teaches devices and methods for detecting an analyte in salivary fluid. U.S. Pat. No. 7,947,508 B2 to Tricca et al. teaches an oral appliance for intra-oral detection or diagnosis of a body condition, or delivery of a substance (e.g., drug delivery) to an individual. Li, C-Y et al. teach a removable artificial tooth to recognize and monitor oral activities, including eating (chewing) and drinking, and to detect bacteria in saliva and monitor oral hygiene (Sensor-Embedded teeth for Oral Activity Recognition. ISWC'13, Sep. 9-12, 2013; Zurich, Switzerland, pp 41-44).

US 2014/0349256 A1 filed by Connor broadly discloses a device and system for monitoring a person's food consumption. A camera in a mobile or wearable device is used voluntarily or passively to image and identify a food, and movements are detected by a wearable sensor, such as a smart watch or bracelet, to determine probable "interactions", i.e., consumption of food. A wireless computer interface is used to collect data and determine intake. Connor teaches that a device comprising a sensor can be worn on or attached to a part of a person's body, including mouth or upper palate. A food-identifying sensor can be a specific nutrient sensor (e.g., glucose, cholesterol, fat, protein, amino acid) or any of a variety of other types of sensors (e.g., electrochemical, biochemical, membrane, pH, osmolality, etc.). A micro-sampling sensor can continuously and/or automatically extract and analyze micro-samples of intraoral fluid. US 2015/0126873, also by Connor, is primarily drawn to analyzing food composition by spectroscopy and sending data to a smart mobile device to monitor intake of foods or individual ingredients or nutrients and communicate information to/with a healthcare professional.

Despite advancement in understanding of the sense of taste and efforts to sense or monitor food or nutrient intake, there is still a need for a wearable or implantable device to replicate or restore taste sensing in the oral cavity of an individual with gustatory impairment.

SUMMARY OF THE INVENTION

An exemplary embodiment of the invention is to provide a system and method to sense and monitor substances within the oral cavity of a subject who is unable to detect or identify such substances due to an impaired sense of taste. Other embodiments of the invention provide a wearable or implantable device to compensate for an impaired sense of taste in a subject. Some embodiments of the invention provide a wearable or implantable device to restore at least one aspect of taste in an individual with gustatory impairment.

An exemplary embodiment of the present invention is a system and method to recreate, simulate, and/or mimic a sense of taste in a subject.

Another embodiment is a system that permits direct implantation and interfacing with the gustation pathways and centers of the brain, the chorda tympani nerve as a particular example, for a renewed or improved perception of taste. In another embodiment, the invention provides a method to detect tastants in the oral cavity and transmit signals to the central nervous system when the taste receptor cells are absent or not functioning, at least in part, and to train a subject by applying electrical stimulation to the subject's gustatory centers. Different patterns of taste sensing are thereby generated which represent the sense of taste in a subject. Once a subject has been trained, the system is usable by a subject to detect or correctly identify one or more tastants, and to recognize that a particular food or nutrient has been ingested.

Another embodiment is a gustatory implant system including (1) a sensor array, (2) a processor, (3) a transmitter, (4) a receiver-stimulator, and (5) an implantable electrode array. The gustatory implant system generates taste maps by detecting tastes with an array of chemical sensors and transmitting variable spatiotemporal stimulation patterns by an electrode array with electrode stimulating points positioned at different locations about the chorda tympani nerve or other part of the gustatory pathways and brain centers. Different patterns of activity in the gustatory centers are thereby generated which mimic the sense of taste in a subject. Once a subject is trained, the system is usable by the subject to detect or correctly identify one or more tastes.

Other embodiments may be used to monitor the concentrations and amounts over time, of substances such as salts, sugars, or other materials which may have health implications for individuals with hypertension, diabetes, metabolic diseases, or other maladies. In other embodiments, specialized sensors and software applications enable a subject or a healthcare professional to monitor intake or exposure for the purpose of medical use, safety, and/or as an adjunct to activities of daily living (ADLs), for instance, oral hygiene and food preparation and intake.

In particular embodiments, the intra-oral sensor device is fabricated or embedded within an ultrathin, flexible and stretchable material and can be integrated with or be removable from maxillary appliances for insertion within the mouth. In other embodiments, the intra-oral sensor device is housed in a dental implant, such as an artificial tooth or teeth or other dental appliance. The intra-oral device comprises at least one sensor able to detect at least one tastant in saliva or other suitable solution. In particular embodiments, signals from the intra-oral device are transmitted wirelessly to a receiver able to apply stimulus to nerve fibers in the chorda tympani nerve. In other embodiments, signals from the intra-oral device are transmitted wirelessly to an external electronic device, particularly a handheld device such as a smart phone, watch, tablet or laptop computer, or to a desk-top or mainframe computer, which is able to process signal data, display real-time information, and trigger alerts if excessive tastants are ingested or undesired or unsafe substances are detected.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION

Figure 1:
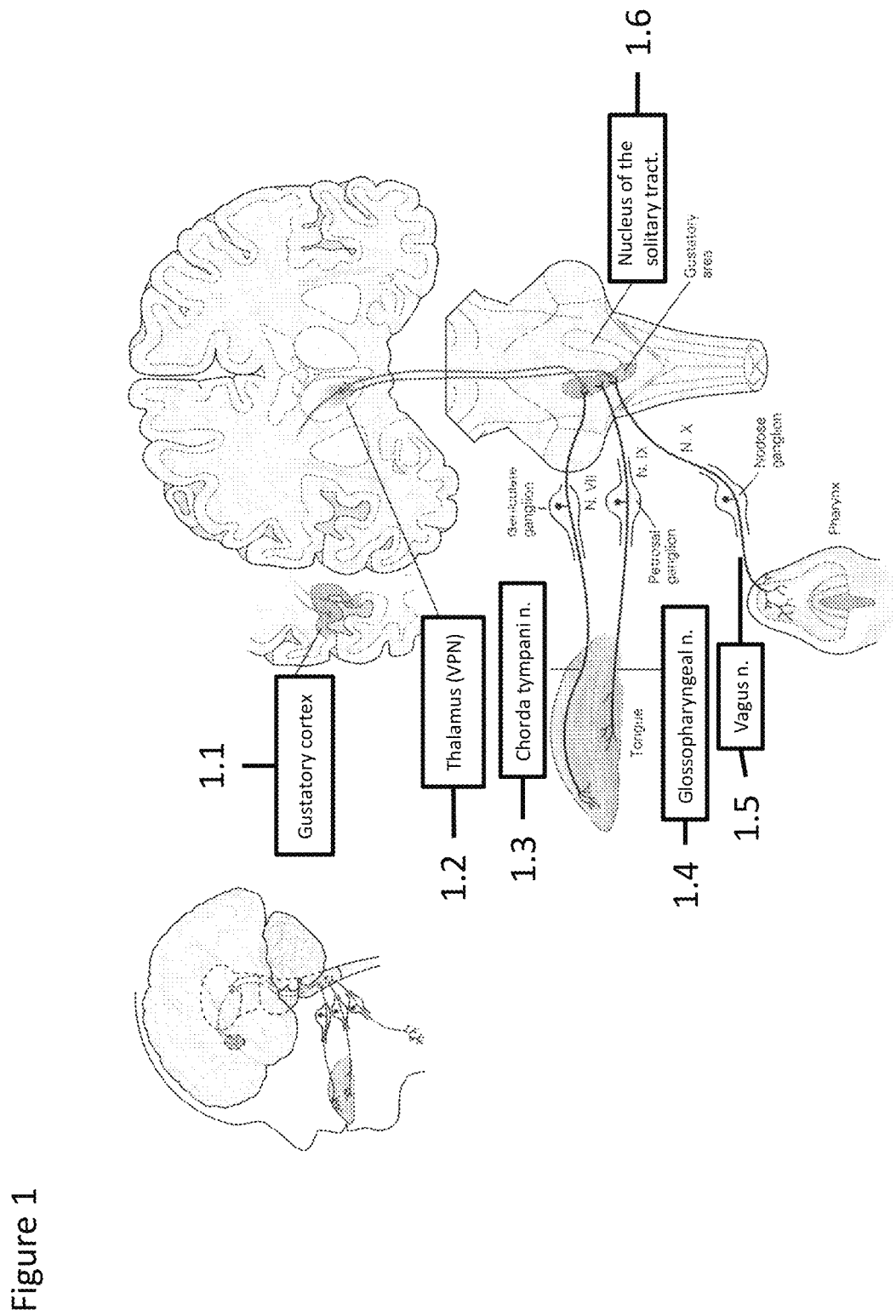
FIG. 1 shows basic neurophysiology of a gustatory system, in particular, the gustatory cortex 1.1, thalamus (VPN) 1.2, chorda tympani n 1.3, glossopharyngeal n. 1.4, vagus n. 1.5, and nucleus of the solitary tract 1.6.

Referring now to the drawings, and more particularly to FIG. 1, there is shown a schematic of basic neurophysiology of the human or animal gustation system, wherein information regarding taste is transmitted from the taste buds to the cerebral cortex via synapses in the brain stem and thalamus. Signals carried by fibers that innervate the taste buds travel through several different nerves to the gustatory area of the nucleus of the solitary tract, which relays information to the ventral posterior medial nucleus of the thalamus. Neuronal projections from the thalamus transmit taste information to the anterior insula-frontal operculum of the gustatory cortex.

Gustatory receptors are located in the gustatory epithelium in the oral cavity. When tastant molecules dissolved in saliva bind to taste receptors capable of receiving one or more particular tastants, gustatory information from the activated taste receptors is passed via the projecting nerve fibers to the nucleus of solitary tract. Different taste receptors subtypes are distributed within regions that have been mapped on the tongue and elsewhere in the oral cavity. Information from the receptors creates unique spatial neurological activity patterns of neural activity for different tastes called taste maps. Different tastants generate different patterns of neural activity. As stimulation of the receptors occurs in continuous time, the taste maps are spatiotemporal patterns which provide the gustatory system means to reproducibly discriminate between different tastes. The neural activity patterns in the nucleus of solitary tract are transmitted to higher levels of the brain (thalamus and anterior insula-frontal operculum or gustatory cortex). Unique spatial neurological activity patterns of neural activity for different tastes (i.e., taste maps) are not limited to the tongue. Taste maps of nervous system structures, in particular regions and parts of the gustatory cortex, may be utilized in accordance with the invention. As used herein, "gustatory cortex" is meant to include, but is not limited to, one or more of chorda tympanic nerve, glossopharyngeal nerve (cranial nerve IX), facial nerve (cranial nerve VII), greater superficial petrosal nerve, vagus nerve (cranial nerve X), geniculate ganglion, petrosal ganglion, nodose ganglion, nucleus of solitary tract, ventral posterior medial nucleus of the thalamus, and anterior insula-frontal operculum. While some exemplary embodiments herein discuss stimulation of the chorda tympani in particular, these are but illustrative examples, and one or more other parts of the gustatory system and cortex may alternatively or additionally be stimulated for simulating or mimicking a taste.

An exemplary gustatory system of the invention comprises three major components that are worn by a subject, including 1) one or more device able to be worn or implanted in the oral cavity, comprising sensors and microelectronics that transmit signals to 2) a programmable microprocessor located near the ear canal to receive signals from the sensors and send electrical currents to 3) an array of stimulating electrodes that make contact with the chorda tympani nerve fibers located in the middle ear. In some embodiments, a fourth component may be used for the purpose of training a subject who will be using the three major wearable or implantable components. Signals from the intra-oral component can be received by a fourth component, which is an external electronic device programmed and configured to process and display data, and further able to transmit signals back to 2) a programmable microprocessor located near the ear canal to receive signals from the electronic device and send electronic currents to 3) the array of stimulating electrodes.

In some embodiments, a stimulatory pattern may be generated in response to a signal received from an intra-oral sensor (received at, e.g., an external electronic device with a programming interface) with or without detection of a tastant profile or fingerprint regularly associated with that tastant or stimulatory pattern. For example, despite a salt tastant not being present and therefore not being detected by the sensor array, a user may command or instruct the implant system to nevertheless stimulate the gustatory cortex (e.g. the chorda tympani) to simulate or mimic the perception of salty. This feature may be desirable if, for example, a user is consuming a bland food and selective simulation or enhancement of flavor is desired. An input from the user can be received by the implant device which prompts stimulation such that one or more tastes or flavors not appreciably present in the food are perceived by the user. A user may choose which tastes are simulated.

Figure 2:
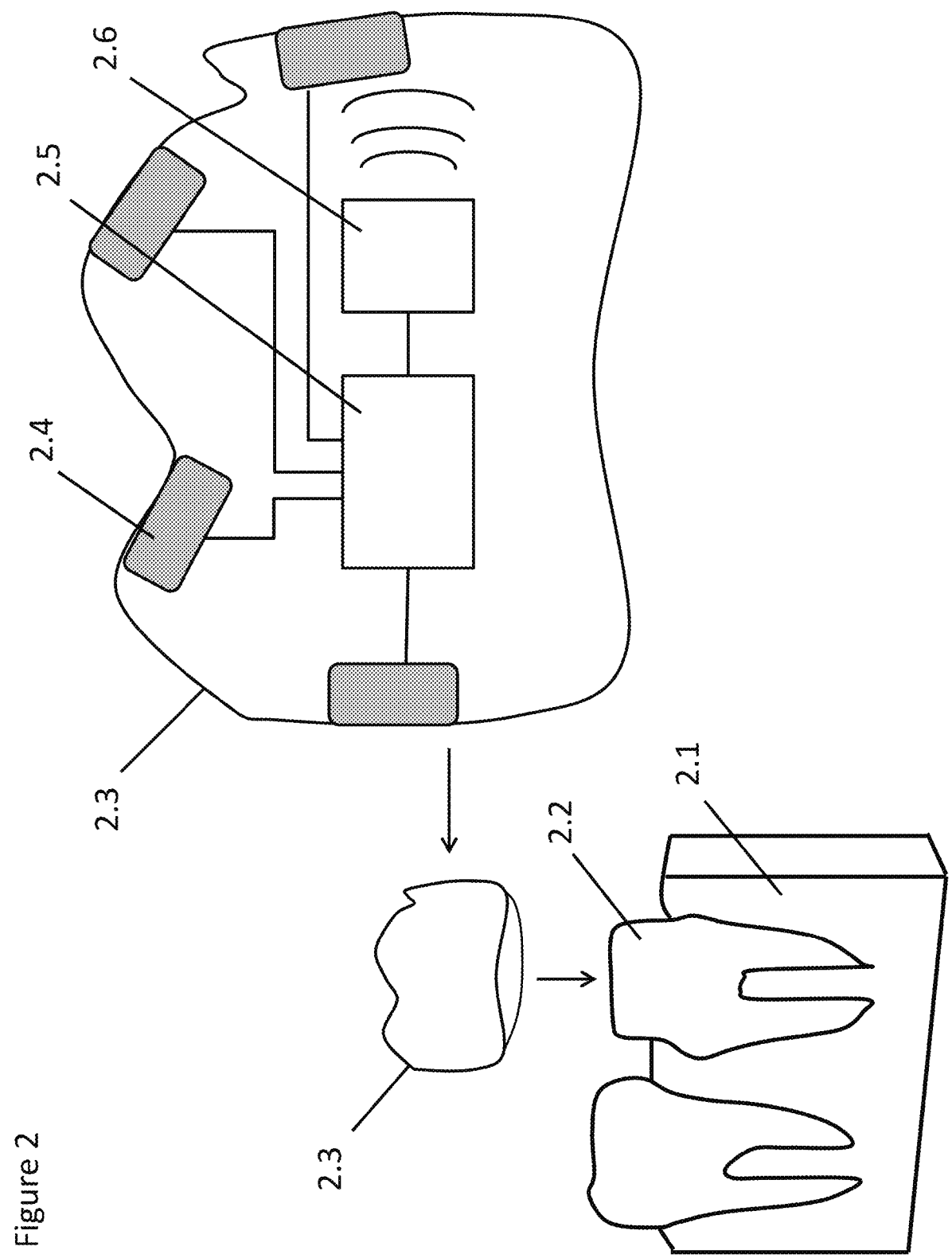
FIG. 2 is a schematic of a gustatory implant and electronic components for sensing a tastant in an oral cavity.

FIG. 2 illustrates an embodiment of an intra-oral component or device, which in this case is a tooth cap (crown) prosthetic implant 2.3. The crown 2.3 is cemented onto a tooth 2.2 so that the sensors are above the gum tissue 2.1. Chemical sensors 2.4 that detect taste molecules (e.g., salts, sugars, acids, etc.) are positioned near the surface of the implant. An oral appliance may also be in the form of a dental bridge, and dental implant, an artificial tooth, a dental appliance, a maxillary appliance, or other device designed to fit in the oral cavity. The oral appliance can be implanted permanently, for instance, it could be cemented in place or implanted in the jaw using any conventional methods known for implanting a replacement tooth or section of teeth, a crown, or a dental implant. Alternatively, it may be placed in the oral cavity temporarily, or it may be configured to be removable, such as partial or full plate dentures would be.

Figure 3:
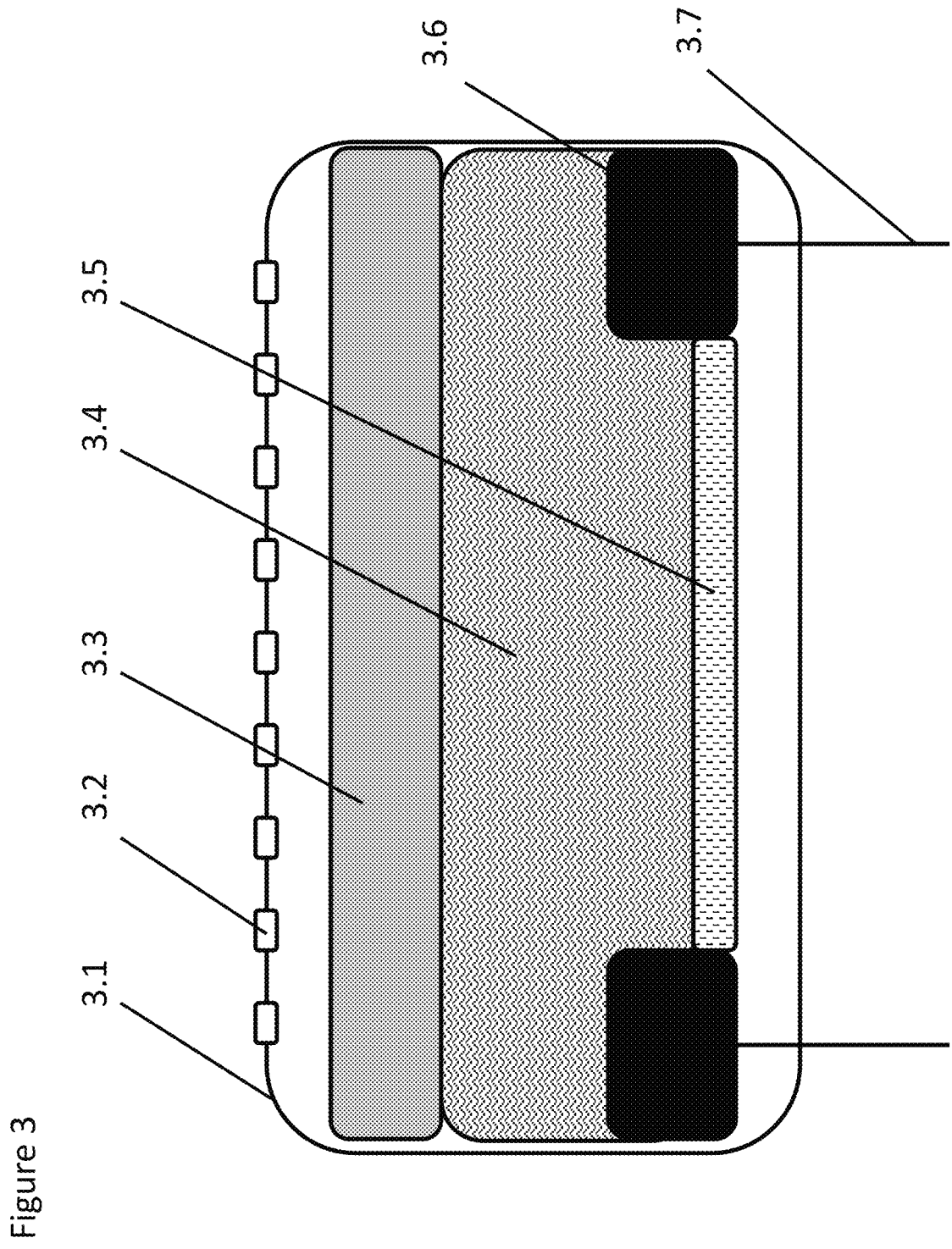
FIG. 3 is a schematic of a single tastant sensor.

Referring now to FIG. 3, chemical sensor 3.1 is an embodiment of a chemical sensor that can be incorporated into an implantable device for an oral cavity, such as the one illustrated in FIG. 2. Small openings 3.2 at the surface of chemical sensor 3.1 allow solutions in the oral cavity to flow in and out of chemical sensor 3.1. A diffusion barrier 3.3 modulates the rate at which molecules can access the conducting substrate layer 3.4. Substrate layer 3.4 is composed of small conducting particles interspersed with a matrix of polymers that expand and contract when they interact with the solute or tastant. Expansion increases the spaces between the conducting particles and results in a decrease in current flow between two electrodes 3.6. The electrodes 3.6 are separated by insulating material 3.5. Sensor 3.1, or an array of sensors 3.1 or other sensor types, are connected to other microelectronic components by small wire leads 3.7.

Referring again to FIG. 2, chemical sensors 2.4 are connected to a microelectronics module 2.5 embedded in the crown. The microelectronics module 2.5 converts changes in sensor currents to digital output signals. A small RF transmitter 2.6 sends the output signals from sensor 2.1 in the oral cavity to an external receiver-microprocessor component located near the ear.

Figure 4:
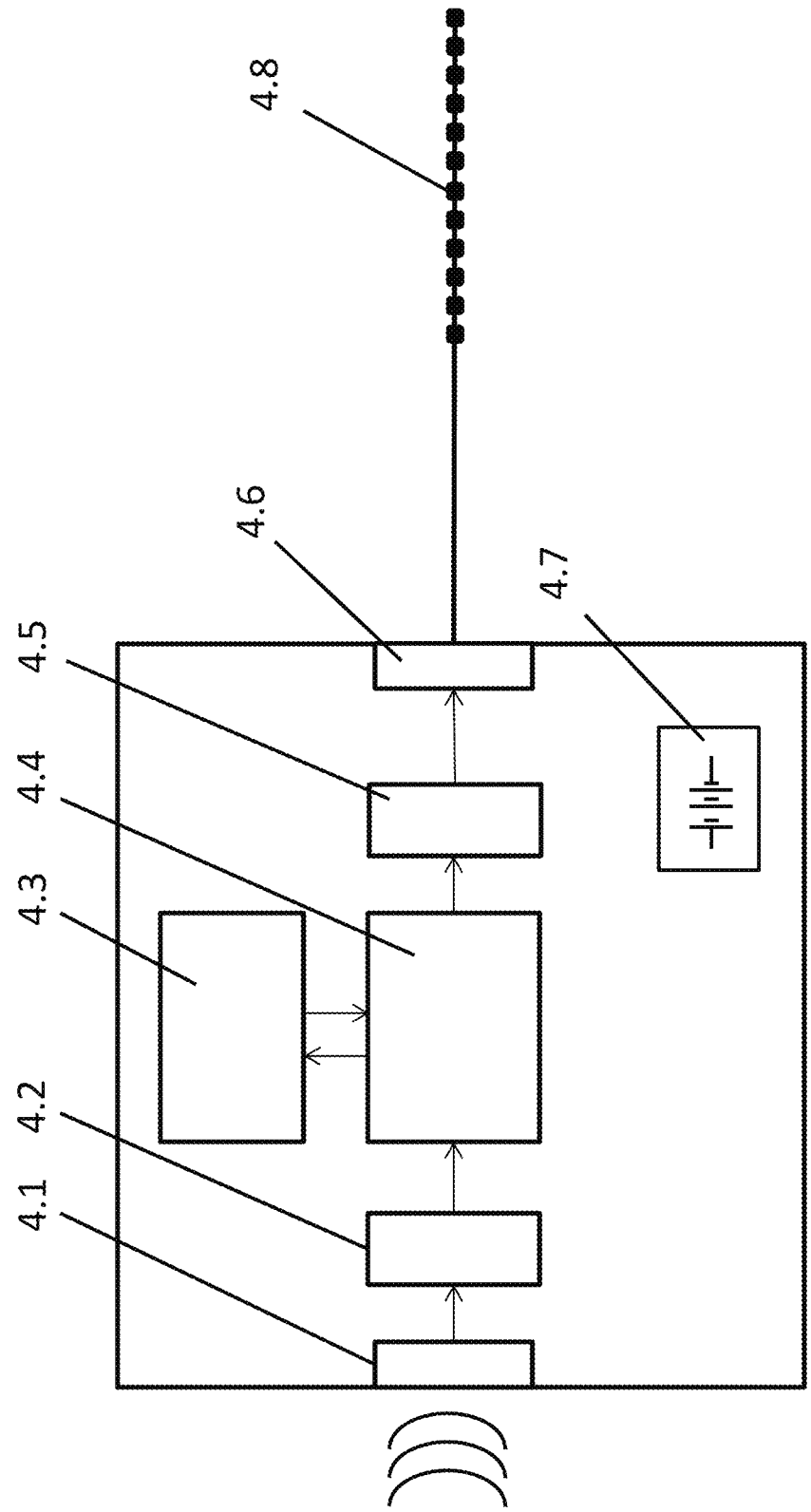
FIG. 4 illustrates a receiver comprising microprocessor components and connections to an electrode array.

An embodiment of an external microprocessor is illustrated in FIG. 4, showing a receiver with microprocessor components and connections to an electrode array. A receiver-decoder 4.1 processes sensor data and stores it in input buffer 4.2. Sensor data is then processed by a central processing unit 4.4 and, using an external programming module (not shown), stores the gustatory sensor fingerprint (integrated responses from multiple sensors) for each taste substance (e.g., NaCl=salty, HCl=sour, sucrose=sweet) in a memory unit 4.3. Stimulus parameters for an electrode array 4.8 are also stored in memory along with perceived taste sensations for different stimulus parameters (electrodes, pulse intensity, duration). For training purposes, a lookup table is used to compare the taste sensor fingerprints for different chemicals to the stimulus parameters needed to generate the appropriate taste perception. These parameters are loaded into an output buffer 4.5 and sent to a stimulus signal generator-driver module 4.6. By stimulating different electrode positions that contact different nerve fibers, different taste sensations are generated, and the subject can be trained to correctly pair a tastant with a taste perception.

In some embodiments, the receiver connected to an electrode array is housed in an implantable device, similar to one used for a cochlear implant to restore the sense of hearing. In other embodiments, the electrode array comprises a wearable device, similar to a hearing aid, or it may be incorporated into a frame such as one might use for eyeglasses to correct a vision defect.

Figure 5:
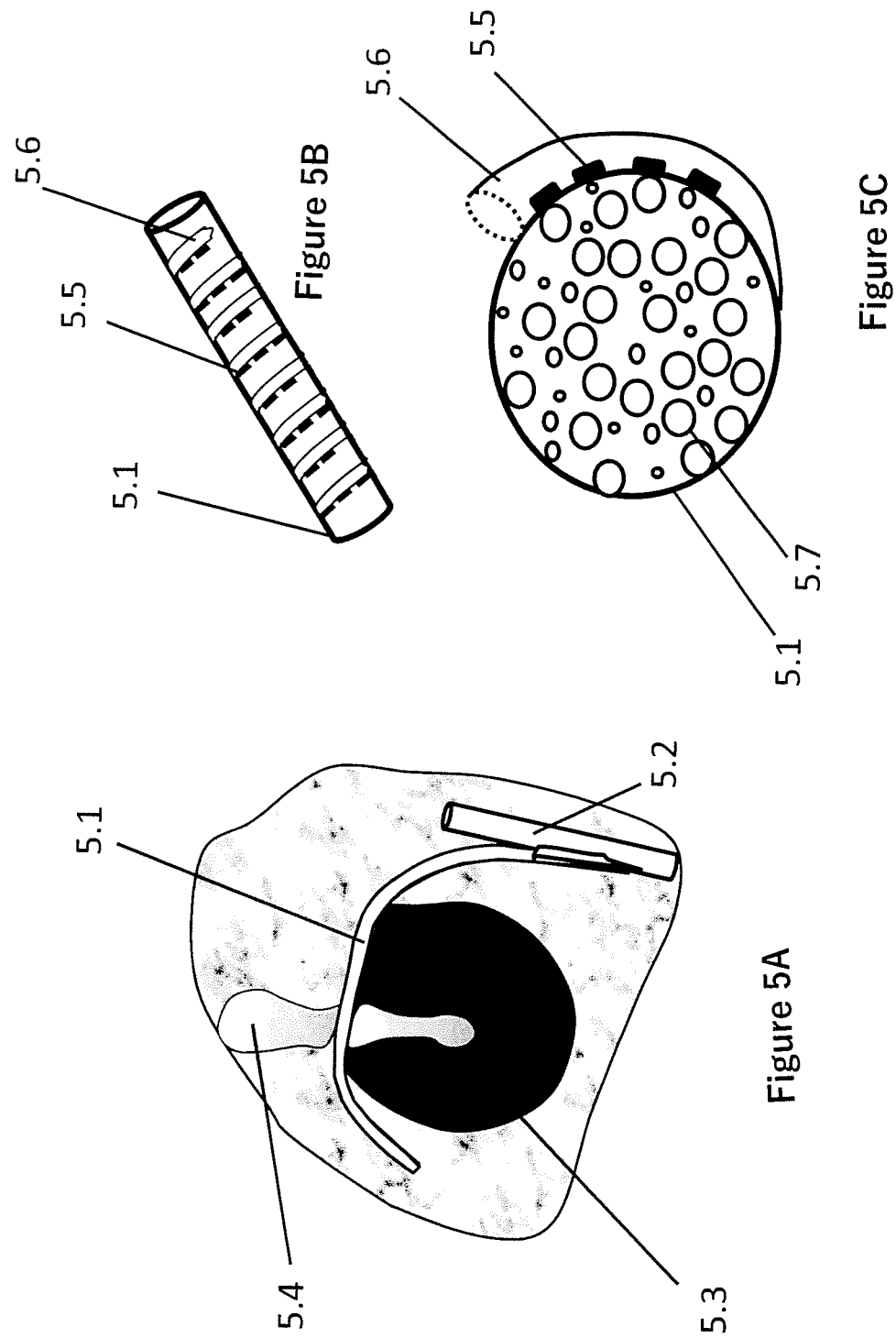
FIG. 5A illustrates human anatomy of the chorda tympani and facial nerves as they pass across the tympanic membrane.
FIG. 5B shows an electrode array in contact with a chorda tympanic nerve.
FIG. 5C shows a cross-section of an electrode array in contact with a chorda tympanic nerve.

FIG. 5A illustrates the anatomy of the chorda tympani nerve 5.1, a branch of the facial nerve 5.2, which passes across the ear drum (tympanic membrane) 5.3 within the inner ear at a location near the head of the malleus bone 5.4. FIGS. 5B and 5C show an electrode array 5.6 consisting of multiple contact points 5.5 with the chorda tympani, longitudinally and in cross-section, respectively. An electrode simulation processor is used to send stimulus pulses to different electrodes in an electrode array 5.6, each contacting a different set of individual taste nerve fibers 5.7. Delivery of the electrical current pulses to individual taste nerve fibers 5.7 generates taste perceptions that are mediated through the nucleus of solitary tract to the ventral posterior medial nucleus, which in turn projects to the gustatory cortex in the anterior insula-frontal operculum (see FIG. 1).

The perception experienced (salt, sweet, sour, etc.) is recorded and programmed along with parameters in a MPU. Memory can be used to generate a particular taste sensation. A lookup table is then used to match the sensor input data (taste quality) with the electrode parameter data (perceived taste). Thus when the sensor detects a tastant for which a taste profile has been recorded, e.g., salty, the appropriate stimulation can be applied via the electrode array to elicit a "salty" taste sensation or experience during a training session.

Figure 6:
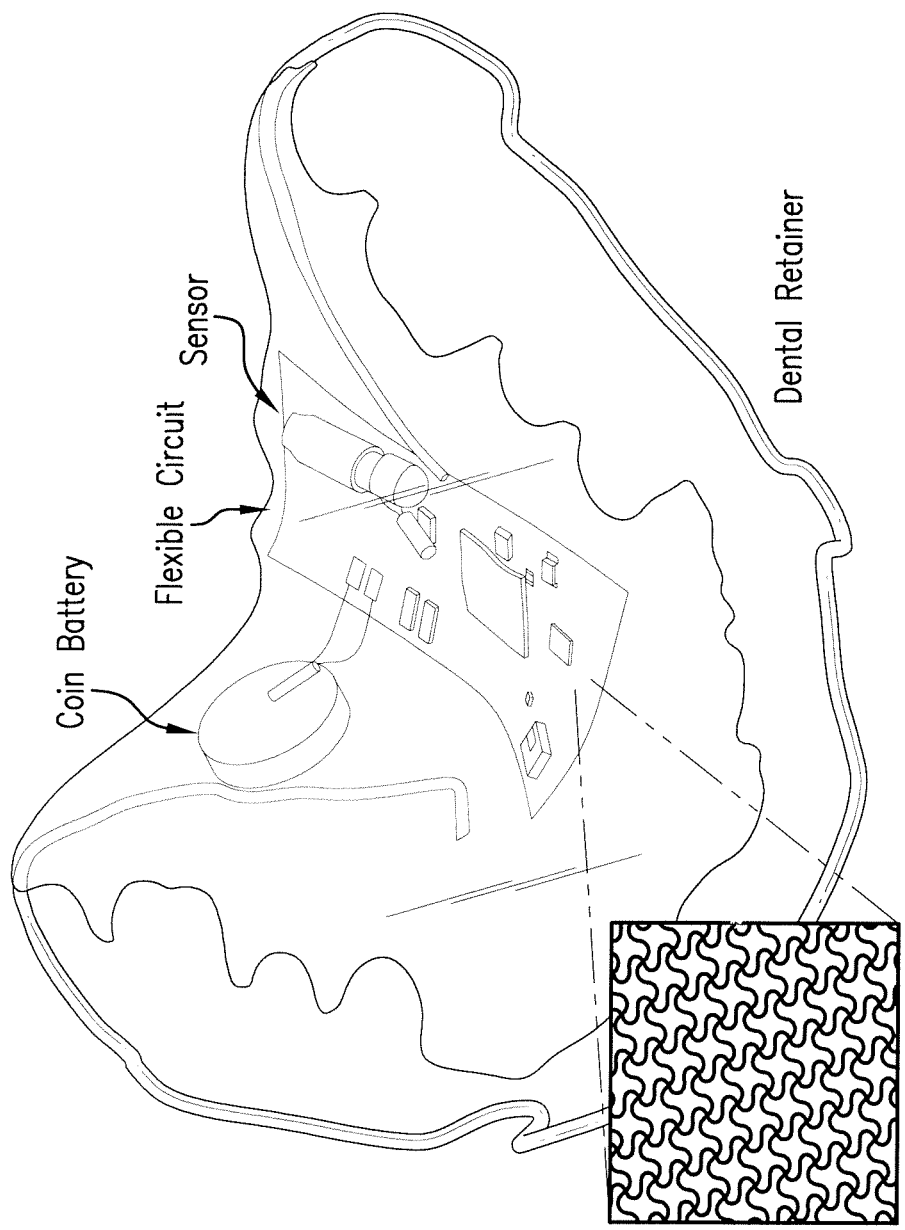
FIG. 6 shows an embodiment of an intra-oral device comprising at least one sensor to detect at least one tastant type and electronic components that process and wirelessly transmit sensing data.
Figure 7:
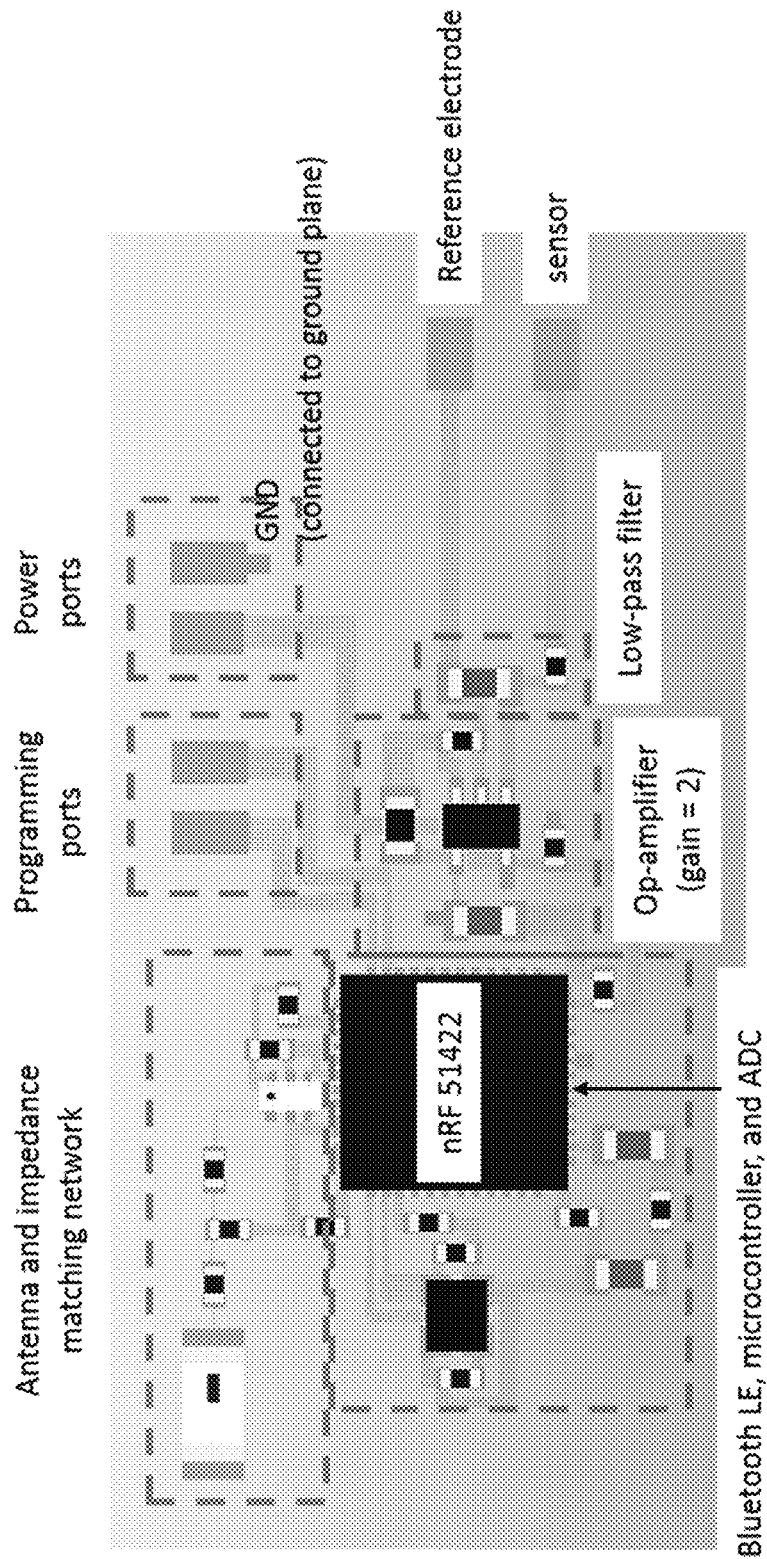
FIG. 7 shows a schematic circuit diagram of microinterconnects and chip components in an intra-oral device for sensing a tastant based on pH.

FIG. 6 illustrates an embodiment comprising a maxillary device commonly used in dental or orthodontic practice and known as a retainer. At least one low-profile sensor and nano-/micro-components can be embedded in the synthetic material that will appose the hard palate when deployed in the oral cavity. Such a device can be easily tolerated by most users and will be relatively unnoticeable and comfortable when in place. The materials are amenable to incorporation of nano-/micro-components that are required for sensing tastants, and the flow of liquids through the oral cavity allow sampling by the sensors embedded in the device. FIG. 7 is an illustration of one of many possible arrangements of nano-/micro-components and connectors for sampling tastants and transmitting data to a receiver. Examples of electronic components include but are not limited to at least one sensor, antenna, balun filter, programming port, crystal oscillator, Bluetooth-enabled chip, operational amplifier, and coin-cell battery.

Figure 8:
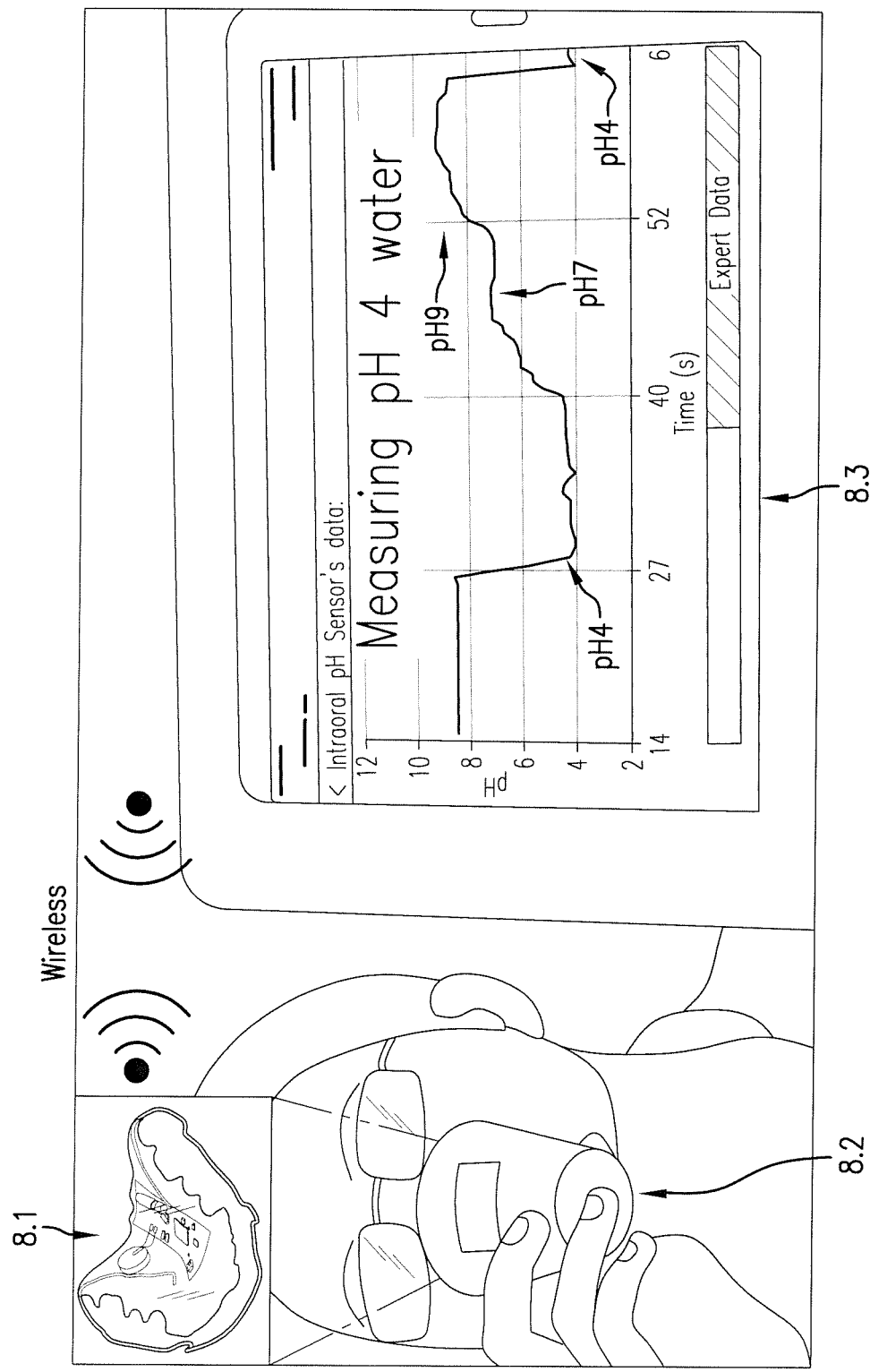
FIG. 8 shows a human subject who wears a wireless taste sensor in the oral cavity for in vivo demonstration of sample solution intake. An external tablet device with a software application receives real time data from the taste sensors in the oral cavity via wireless transmission and displays the data on the electronic device.

FIG. 8 is illustrative of a system for identifying tastants and transmitting data to a device programmed and configured to process and display data. Element 8.1 shows a human subject wearing an intra-oral device with an implantable device for sensing at least one tastant in the oral cavity. Element 8.2 shows a sample solution containing a tastant of interest to be inserted in the oral cavity and sampled by sensors in the implantable device. Data from the sensor and micro-components (see FIG. 7) is transmitted wirelessly to electronic device (e.g., tablet) 8.3, where it is processed and displayed on a screen for the user to read.

In some embodiments, data is transmitted to an external electronic device, a healthcare practitioner can act as an "instructor" by directing stimulation of the gustatory cortex via application of electrical impulses to specific subsets of chorda tympanic nerve fibers.

In some embodiments, data received from the oral cavity of a subject is transmitted directly to the gustatory cortex via a receiver enabled to provide electrical impulses to a chorda tympanic nerve in the same subject.

Figure 9:
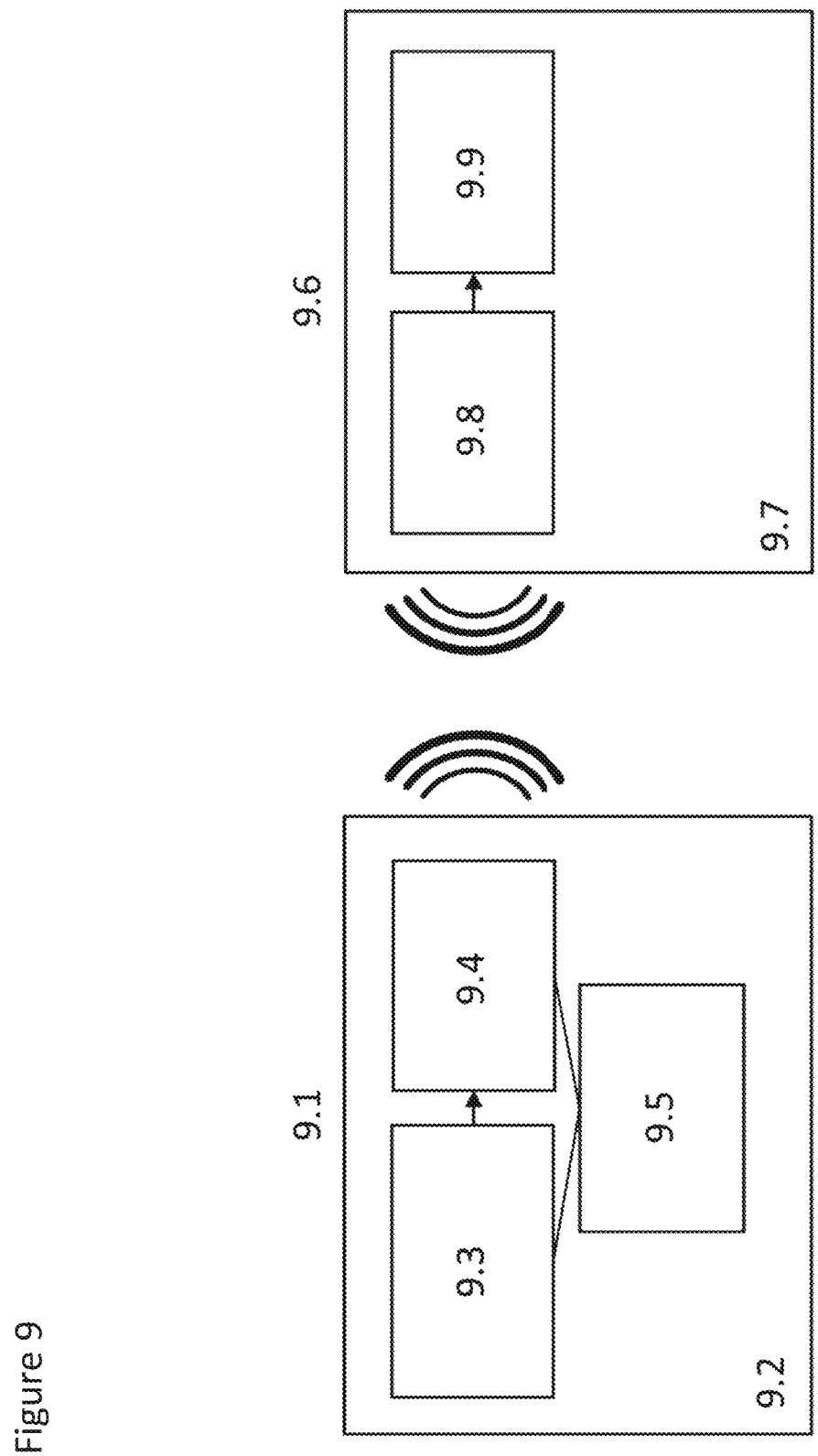
FIG. 9 shows schematic diagrams illustrating the principle components of a sensing device for wireless sensing a taste solution and a receiver for data acquired via the sensing device.

FIG. 9 shows schematic diagrams illustrating the principle components of the sensing device 9.1 and the receiver 9.6 for display of wireless data on an electronic device. The wireless electronics of sensing device 9.1 is inserted into the oral cavity through integration with an oral appliance, including but not limited to a dental bridge, dental implant, crown, artificial tooth, dental appliance, maxillary appliance, or other device designed to fit in the oral cavity. An array of electrochemical sensors 9.2 record data from tastants and transmits the data to external portable electronics 9.6 through a wireless Bluetooth-enabled transmitter 9.4. A small rechargeable battery 9.5 powers the sensors 9.3 and telecommunication units 9.4 in the sensing device 9.1. The wirelessly transmitted signals are detected and recorded by smart electronics 9.7 in the external system 9.6. The wireless Bluetooth-enabled receiver 9.8 acquires signals and the software application interface 9.9 processes, displays and stores the data.

Figure 10:
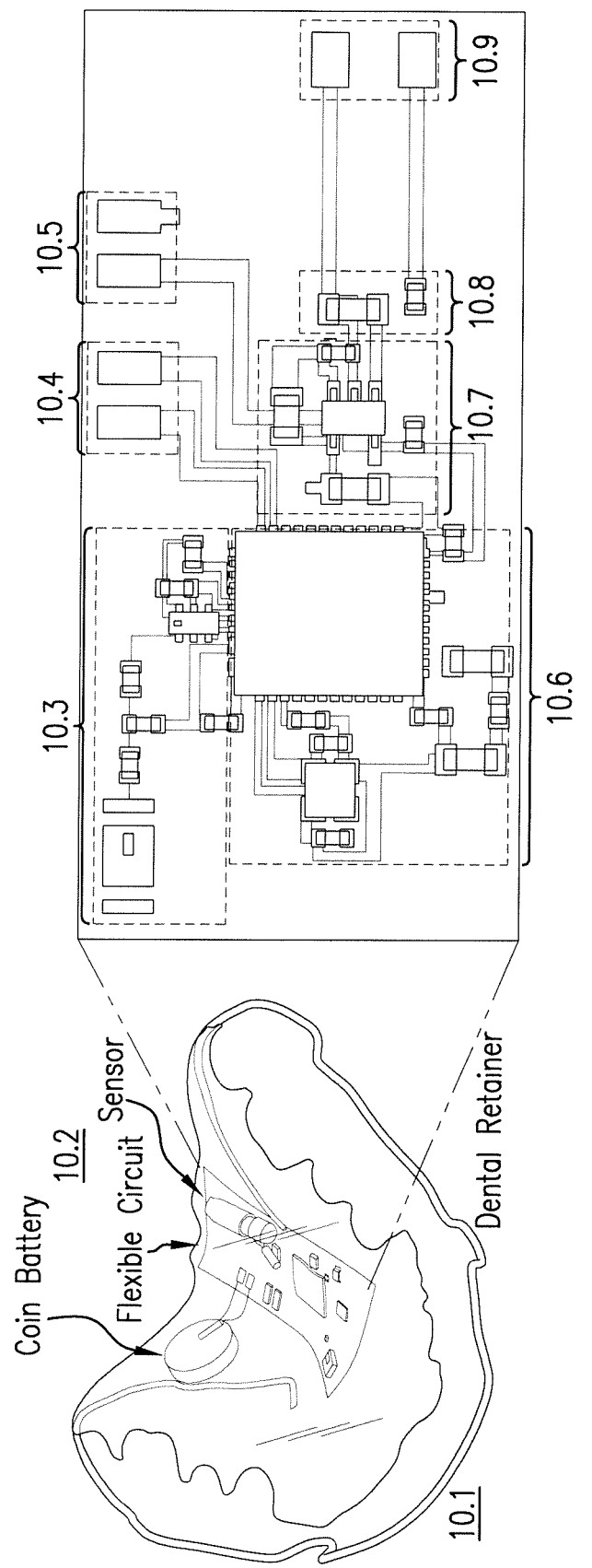
FIG. 10 shows an embodiment wherein (left panel) a sensor device is integrated into a removable dental retainer (e.g., maxillary appliance), and (right panel) a schematic drawing illustrates components of the appliance, which are configured to measure one of tastes and transmit data wirelessly to a receiver, comprising electrochemical sensors, a voltage regulator, a Bluetooth-enabled wireless unit having a microcontroller and RF transmitter/receiver, antenna, band-pass filter, crystal oscillator and a coil cell battery.

FIG. 10 shows (left panel) a dental retainer 10.1 embedding an intraoral sensor device 10.2 comprising sensors and wireless telemetry components, as diagrammed (right panel). The device comprises an antenna and signal impedance matching network 10.3 for transmitting signals, programming ports 10.4 for manipulating the micro-controller, power ports 10.5 for connecting a coin cell battery, Bluetooth-enabled wireless unit 10.6 having a Bluetooth low energy chip, micro-controller, and analogue-to-digital converter, operational amplifier 10.7 for amplifying the signals, low-pass filter 10.8 for filtering the raw signals to acquire a specific signal with a desired frequency, electrochemical sensors 10.9 for measuring at least one of five different tastes (salt, sweet, sour, bitter and umami).

Figure 11:
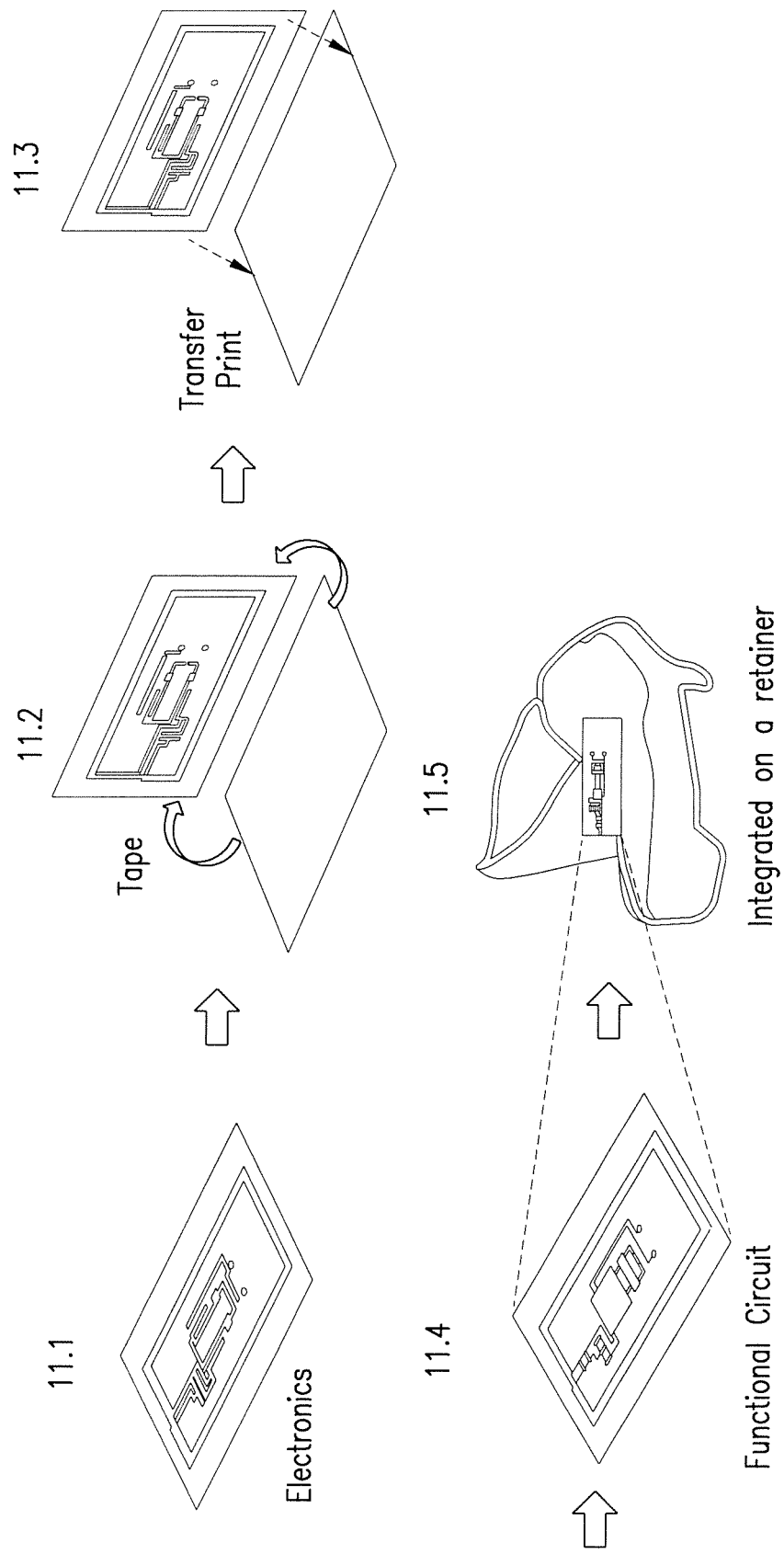
FIG. 11 shows schematic illustrations of the fabrication process used to develop a sensing device by using the combination of the conventional, wafer-scale microfabrication technique and material's transfer printing.

FIG. 11 shows an exemplary process for fabricating a sensing device. Overall, the fabrication combines a technique of material's transfer printing and conventional wafer scale microfabrication techniques to define the electronics, including meander patterns (electrodes, interconnects, and supporting posts) on a silicon wafer, including but not limited to multiple steps of metallization, photo lithography, and metal etching (11.1). Once electronics are defined, a nanomaterials transfer printing technique retrieves it from a wafer using a water-soluble tape (11.2). During this process, a key will be to have a sacrificial polymer layer between a silicon wafer and patterned electronics. When the polymer layer is dissolved in a chemical solution, the electronics can be attached to water-soluble tape. Afterwards, electron beam metal evaporation will deposit a 5 nm-thick silica layer at the bottom of the electronics and at the same time, a soft silicone membrane will be activated by ozone exposure to use covalent bonding. The electronics on the tape is transferred onto the ozone-activated elastomeric membrane by dissolving the water-soluble tape (11.3). Then, chip-scale components are selectively bonded to the surface of supporting posts, molded onto the thin elastomeric membrane. Except for these supporters, the chip is suspended in air, which makes it mechanically isolated from the applied stresses and strains. Solder chunk is applied onto the targeted posts and then hard chip components are mounted on the posts. Low-temperature curing allows a strong binding of the components (11.4). The product of this fabrication process can be incorporated into an intra-oral device of any suitable type, including but not limited to a maxillary appliance (11.5).

Target tastants to which the sensor array is sensitive can vary depending on the intended use of the gustatory implant system. For improving quality of life of an ageusic subject, target tastants may include molecules commonly associated with foods, including molecules associated with food or fragrances, such as salt, sweet, sour, bitter and umami. In some embodiments target tastants may include tastes for which humans naturally have no sensitivity. That is to say, the sensor array is not limited to detection of tastants which the natural human gustatory system is capable of detecting. For instance, the system may alert a user to the presence of harmful substances such as an allergen that might cause anaphylactic shock, phenylalanine for a phenylketonuriac, gluten for a person with celiac disease, or any other substances or metabolites that could be injurious to an individual.

The subjects which are the end-users of the methods and devices of the invention are generally mammals, and are usually humans. Veterinary applications of this technology are also contemplated.

One of ordinary skill in the art will recognize that known sensor arrays and even processing for existing sensor arrays may be used in the practice of the invention. In an alternative embodiment, a commercially-available sensor array for detecting tastant molecules may be adapted for use with the present invention.

While processing as herein has been disclosed as mostly or entirely taking place on board a processor, this represents only one exemplary embodiment of the current invention. Processing steps may be divided over a plurality of separate processors which may be external or internal (i.e. implanted in the subject). Processing steps may also be performed remotely, with the sensor array and/or receiver-stimulator in wireless communication with a processor which is not carried or worn by the subject. Furthermore, one of ordinary skill in the art will recognize that all necessary processing may be performed by hardware, software (e.g. computer programs), firmware, or a wide range of combinations thereof and is not limited to the exemplary processor shown in FIG. 8 or disclosed elsewhere herein.

While the invention has been described in terms of preferred embodiments, those skilled in the art will recognize that the invention can be practiced with modification within the spirit and scope of the appended claims.

What is claimed is:

1. A system for mimicking a sense of taste in a subject, comprising:
    a sensor array comprising a plurality of sensors for detecting one or more tastant, said sensor array producing sensor output signals in response to detecting said one or more tastants;
    a processor for processing said sensor output signals into digital encoded information;
    a transmitter for transmitting said digital encoded information transcutaneously into said subject;
    a receiver-stimulator configured to receive said transcutaneously transmitted digital encoded information and generate electrical impulses as a function thereof; and
    an implantable electrode array comprising at least one stimulating electrode configured to stimulate the gustatory cortex in said subject with said electrical impulses,
    wherein each of said at least one stimulating electrode of said implantable electrode array is individually controllable.

2. The system as claimed in claim 1, wherein said sensor array is part of an intraoral device selected from the group consisting of a dental bridge, dental implant, artificial tooth, a crown, dental appliance, full denture plate, partial dental plate, and a maxillary appliance.

3. The system as claimed in claim 2, wherein said intraoral device is a maxillary appliance.

4. The system as claimed in claim 3, wherein said maxillary appliance comprises said sensor array fabricated or embedded within an ultrathin, flexible and stretchable material that can be integrated with or be removable from said maxillary appliance.

5. The system as claimed in claim 1, wherein said electrical impulses are associated with spatiotemporal electrical stimulation patterns in a gustatory cortex.

6. The system as claimed in claim 1, wherein said sensor array comprises a plurality of groupings of one or more sensors, each grouping configured to detect a different tastant.

7. A system for mimicking a sense of taste in a subject, comprising:
    a sensor array comprising a plurality of sensors for detecting one or more tastant, said sensor array producing sensor output signals in response to detecting said one or more tastants;
    a processor for processing said sensor output signals into digital encoded information;
    a transmitter for transmitting said digital encoded information transcutaneously into said subject;
    a receiver-stimulator configured to receive said transcutaneously transmitted digital encoded information and generate electrical impulses as a function thereof; and
    an implantable electrode array comprising at least one stimulating electrode configured to stimulate the gustatory cortex in said subject with said electrical impulses,
    wherein said sensor array comprises a plurality of the same sensor, wherein a different filter is associated with each sensor of said plurality of the same sensor which differentially affects the passage or flow of different molecules across the filter.

8. The system as claimed in claim 1, further comprising at least one recording electrode for recording one or more bioelectric properties of the gustatory cortex in said subject.

9. The system as claimed in claim 8, wherein said at least one recording electrode is an integral part of said implantable electrode array.

10. A system for mimicking a sense of taste in a subject, comprising:
    a sensor array comprising a plurality of sensors for detecting one or more tastant, said sensor array producing sensor output signals in response to detecting said one or more tastants;
    a processor for processing said sensor output signals into digital encoded information;

a transmitter for transmitting said digital encoded information transcutaneously into said subject;

a receiver-stimulator configured to receive said transcutaneously transmitted digital encoded information and generate electrical impulses as a function thereof; and an implantable electrode array comprising at least one stimulating electrode configured to stimulate the gustatory cortex in said subject with said electrical impulses, wherein the implantable electrode array is configured for stimulating a chorda tympani nerve.

11. The system as claimed in claim 1, wherein said processor is an external electronic device selected from the group consisting of smart phone, smart watch, smart table, laptop computer, and computer, wherein said external electronic device is programmed to receive, process and display data, and is further able to transmit a signal to direct said implantable electrode array to deliver an electric impulse for stimulating said gustatory cortex.

12. A system for monitoring ingestion in a subject, comprising:

a sensor array comprising at least one sensor for detecting ingestion of at least one substance selected from the group consisting a food, a food ingredient, a food nutrient, a drug, an oral medication, and an allergen, said sensor array producing sensor output signals in response to detecting said at least one substance, wherein said sensor array comprises a maxillary appliance wherein said sensor array is fabricated or embedded within an ultrathin, flexible and stretchable material that can be integrated with or be removable from said maxillary appliance;

a processor for processing said sensor output signals into digital encoded information;

a transmitter for transmitting said digital encoded information; and an external electronic device selected from the group consisting of smart phone, smart watch, smart table, laptop computer, and computer, wherein said external electronic device is programmed to receive and process digital encoded information, and to display data and provide information to a user that identifies ingestion of said at least one substance, wherein said subject is a patient and said user is a healthcare professional.

13. The system for monitoring ingestion as claimed in claim 12, wherein said external electronic device is further programmed to generate an alarm or message to notify at least one of said subject and said user when said at least one substance has been ingested.

14. The system for monitoring ingestion as claimed in claim 12, wherein said external electronic device is further programmed to generate an alarm or message to notify at least one of said subject and said user when said at least one substance has been ingested at a level in excess of a predetermined quantity or level.

* * * * *